(12) United States Patent
Bates et al.

(10) Patent No.: US 10,093,632 B2
(45) Date of Patent: Oct. 9, 2018

(54) METHODS FOR PREPARING SUBSTITUTED 5,6-DIHYDRO-6-PHENYLBENZO[F] ISOQUINOLIN-2-AMINE

(71) Applicant: ArQule, Inc., Burlington, MA (US)

(72) Inventors: Craig Bates, Pelham, NH (US);
Jianmin Mao, Winchester, MA (US);
David P. Reed, Pelham, NH (US)

(73) Assignee: ArQule, Inc., Burlington, MA (US)

( * ) Notice: Subject to any disclaimer, the term of this patent is extended or adjusted under 35 U.S.C. 154(b) by 0 days.

(21) Appl. No.: 15/800,648

(22) Filed: Nov. 1, 2017

(65) Prior Publication Data

US 2018/0065937 A1    Mar. 8, 2018

Related U.S. Application Data

(62) Division of application No. 15/381,418, filed on Dec. 16, 2016, now Pat. No. 9,834,519.

(60) Provisional application No. 62/268,758, filed on Dec. 17, 2015.

(51) Int. Cl.
*C07D 239/84* (2006.01)
*C07D 239/70* (2006.01)

(52) U.S. Cl.
CPC ......... *C07D 239/84* (2013.01); *C07D 239/70* (2013.01); *C07B 2200/13* (2013.01)

(58) Field of Classification Search
CPC .. C07B 2200/13; C07D 239/70; C07D 239/84
See application file for complete search history.

(56) References Cited

U.S. PATENT DOCUMENTS 6,133,257 A    10/2000   Batchelor et al.
8,357,694 B2   1/2013    Ali et al.

FOREIGN PATENT DOCUMENTS

WO      WO 98/28281 A1      7/1998
WO      WO 2010/078421  *   7/2010  ........... C07D 221/10
WO      WO 2010/078421 A1   7/2010
WO      WO 2012/177852 A1   12/2012

OTHER PUBLICATIONS

Eathiraj, S. et al., "A novel mode of protein kinase inhibition exploiting hydrophobic motifs of autoinhibited kinases", The Journal of Biological Chemisty, vol. 286, p. 20677-20687, 2011.

* cited by examiner

*Primary Examiner* — Erich A Leeser
(74) *Attorney, Agent, or Firm* — Cooley LLP; Matthew Pavao; Chen Chen

(57) ABSTRACT

The present application relates to methods of preparing Compound A:

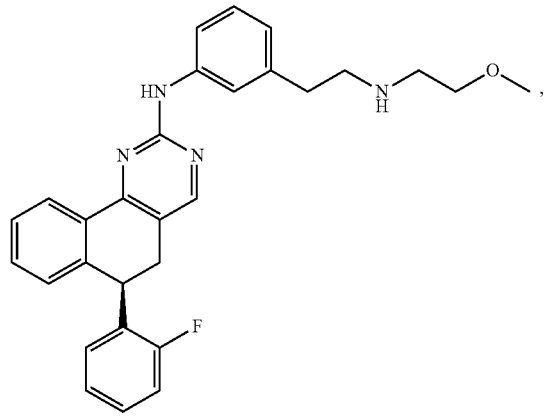

(A)

or a salt thereof, and a polymorph of Compound A dihydrochloride salt:

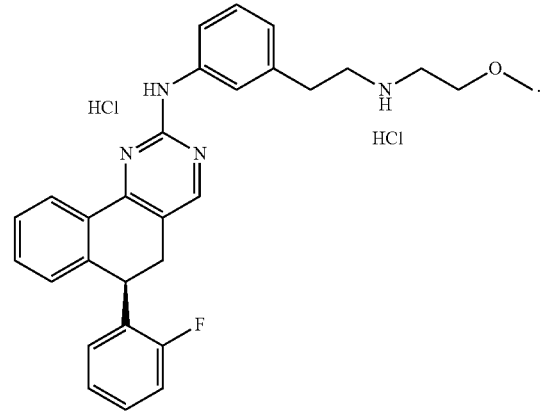

20 Claims, 1 Drawing Sheet

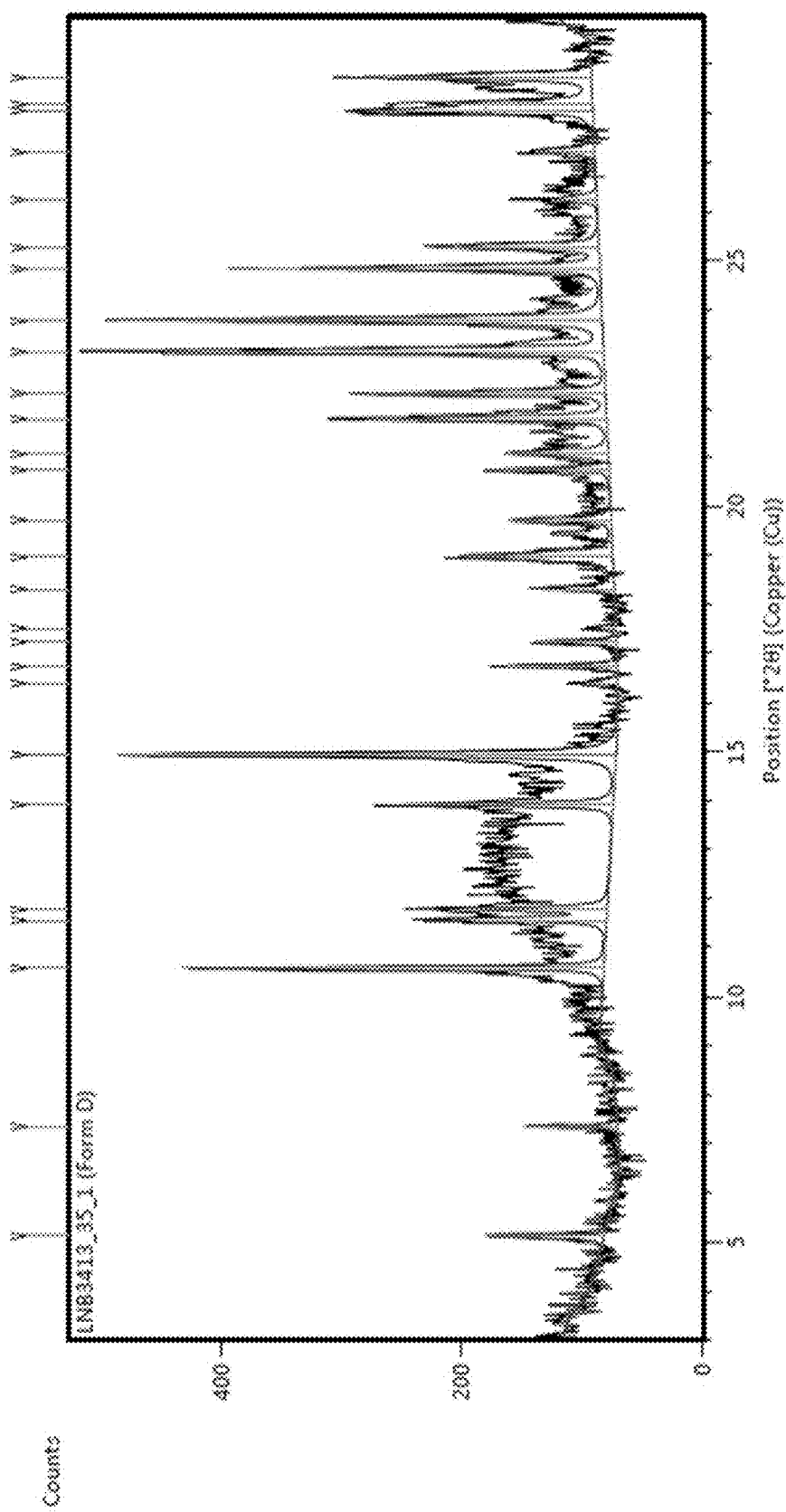

METHODS FOR PREPARING SUBSTITUTED 5,6-DIHYDRO-6-PHENYLBENZO[F] ISOQUINOLIN-2-AMINE

CROSS-REFERENCE TO RELATED APPLICATIONS

This application is a division of U.S. Ser. No. 15/381,418, filed on Dec. 16, 2016 (now allowed), which claims priority to, and the benefit of, U.S. Ser. No. 62/268,758, filed on Dec. 17, 2015, the contents of each of which are incorporated herein by reference in their entirety.

BACKGROUND

Cancer is the second leading cause of death in the United States, exceeded only by heart disease. Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational "mechanisms" may lead to the development of cancer. As such, heterogeneity frequently exists between cancer cells taken from tumors of the same tissue and same type that have originated in different individuals. Frequently observed mutational "mechanisms" associated with some cancers may differ between one tissue type and another (e.g., frequently observed mutational "mechanisms" leading to colon cancer may differ from frequently observed "mechanisms" leading to leukemias). It is therefore often difficult to predict whether a particular cancer will respond to a particular chemotherapeutic agent.

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of cancers.

FGFR2 is a member of the fibroblast growth factor receptor family, where amino acid sequence is highly conserved between members and throughout evolution. FGFR family members differ from one another in their ligand affinities and tissue distribution. A full-length representative protein consists of an extracellular region, composed of three immunoglobulin-like domains, a single hydrophobic membrane-spanning segment, and a cytoplasmic tyrosine kinase domain. The extracellular portion of the protein interacts with fibroblast growth factors, setting downstream signals, ultimately influencing mitogenesis and differentiation.

Alterations in the activity (expression) of the FGFR2 gene are associated with certain cancers. The altered gene expression may enhance several cancer-related events such as cell proliferation, cell movement, and the development of new blood vessels that nourish a growing tumor. The FGFR2 gene is abnormally active (overexpressed) in certain types of stomach cancers, and this amplification is associated with a poorer prognosis and response to standard clinical methods. Abnormal expression of FGFR2 is also found in patients with prostate cancer. More than 60 percent of women with breast cancer in the United States carry at least a single mutation in this gene as well.

Accordingly, new compounds for modulating FGFR2 and treating proliferation disorders, including cancer, and methods for preparing these new compounds (e.g., with a higher yield and/or improved purity, and/or on a larger production scale) are needed. The present application addresses these needs.

SUMMARY

The present application relates to a method of making Compound A:

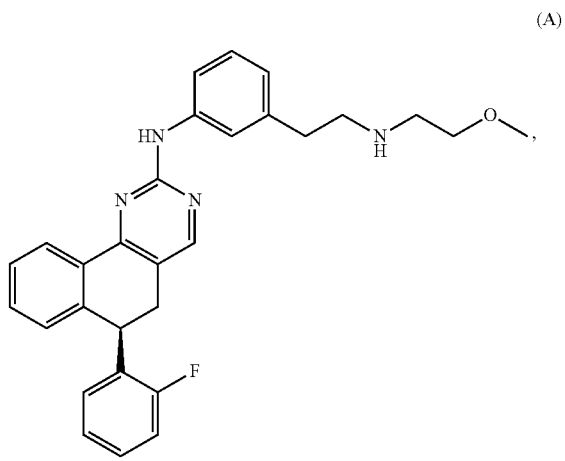 [SMILES: COCCNCCc1cccc(Nc2ncc3c(n2)-c2ccccc2[C@H](c2ccccc2F)C3)c1]

or a salt thereof, comprising one or more steps selected from:

Step 1: reacting Compound 1:

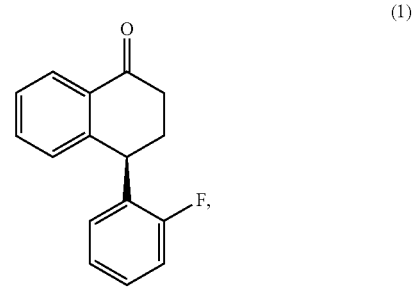 [SMILES: O=C1CC[C@@H](c2ccccc2F)c2ccccc21]

with N,N-dimethylformamide dimethyl acetal (DMF-DMA), to form Compound 2:

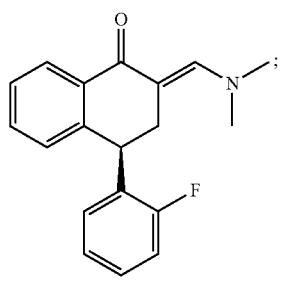
Step 2: reacting Compound 2:
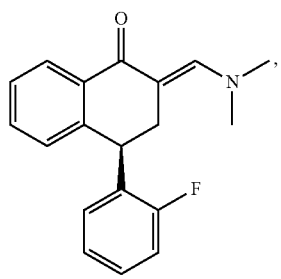
with Compound 3:
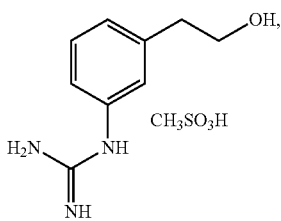
to form Compound 4:
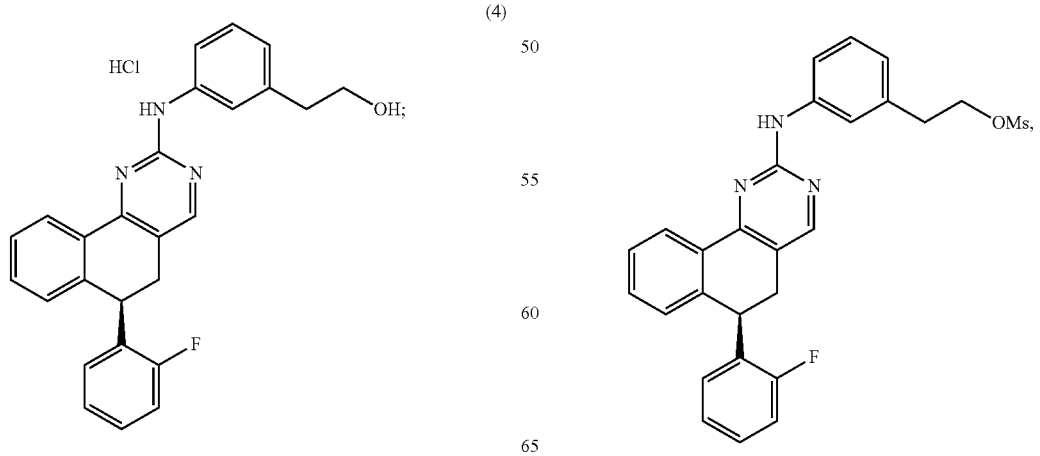
Step 3: reacting Compound 4:
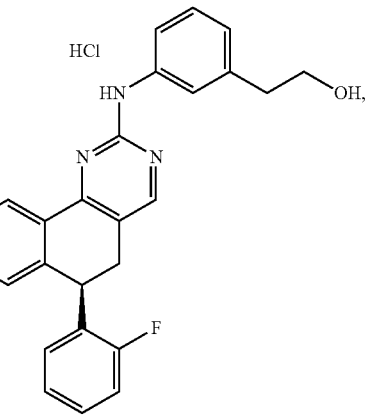
with methanesulfonyl chloride (MsCl) to form Compound 5:
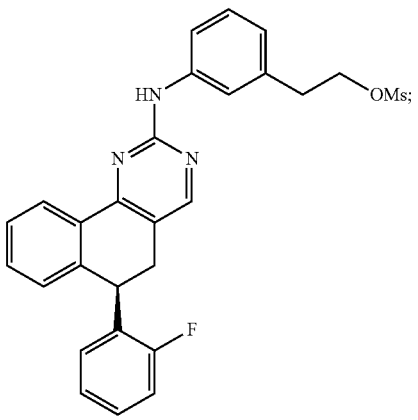
and
Step 4: reacting Compound 5:

with methoxyethylamine to form Compound A:

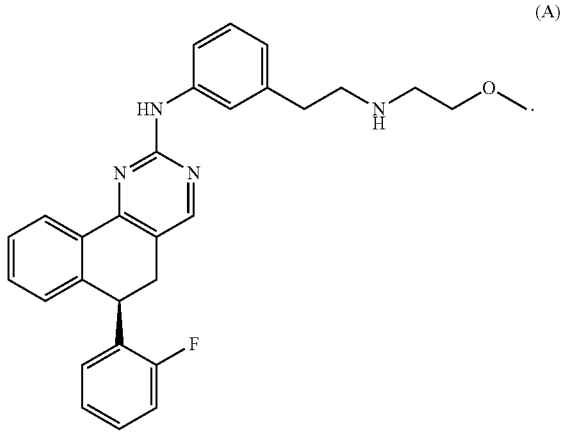 [SMILES: COCCNCCc1cccc(Nc2ncc3c(n2)-c2ccccc2[C@H](c2ccccc2F)C3)c1]
(A)

The present application also relates to a method of making a polymorph of Compound A dihydrochloride salt:

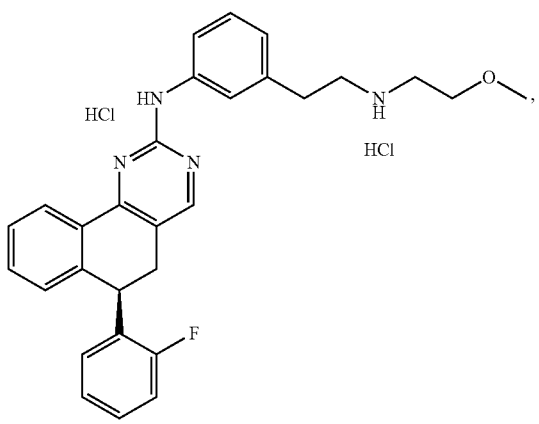 [SMILES: COCCNCCc1cccc(Nc2ncc3c(n2)-c2ccccc2[C@H](c2ccccc2F)C3)c1 ; Cl ; Cl]

comprising reacting Compound A:

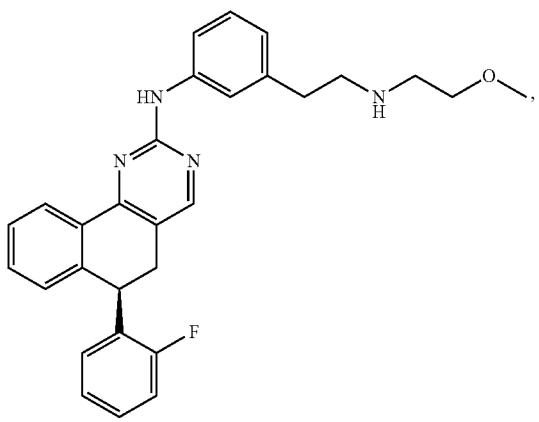
(A)

with HCl to form the polymorph; and optionally recrystallizing the polymorph.

The present application also provides a pharmaceutical composition comprising Compound A or a salt thereof or a polymorph of Compound A dihydrochloride salt prepared by the methods of the present application, and a pharmaceutically acceptable carrier or excipient.

The present application also provides a method of treating a cell proliferative disorder, comprising administering, to a subject in need thereof, a therapeutically effective amount of a composition comprising Compound A or a salt thereof or a polymorph of Compound A dihydrochloride salt prepared by the methods of the present application.

The present application also provides Compound A or a salt thereof or a polymorph of Compound A dihydrochloride salt prepared by the methods of the present application for use in the manufacture of a medicament for treating a cell proliferative disorder in a subject in need thereof.

The present application also provides use of Compound A or a salt thereof or a polymorph of Compound A dihydrochloride salt prepared by the methods of the present application in treating a cell proliferative disorder in a subject in need thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In the case of conflict, the present specification, including definitions, will control. In addition, the materials, methods, and examples are illustrative only and are not intended to be limiting.

Other features and advantages of the disclosure will be apparent from the following detailed description and claims.

BRIEF DESCRIPTION OF THE FIGURES

FIG. 1 sets forth an X-ray powder diffraction pattern of a polymorph of Compound A dihydrochloride salt prepared by the methods of the present application.

DETAILED DESCRIPTION

Methods of the Present Application

The present application provides methods of synthesis of Compound A:

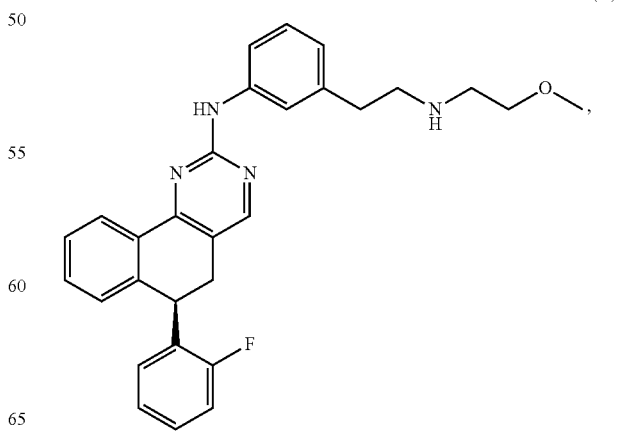
(A)

(R)-6-(2-fluorophenyl)-N-(3-(2-(2-methoxyethyl-amino)ethyl)phenyl)-5,6-dihydrobenzo[h]quinazolin-2-amine or a salt thereof, comprising one or more steps selected from:

Step 1: reacting Compound 1:

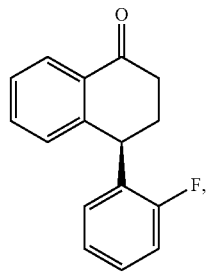
(1)

with N,N-dimethylformamide dimethyl acetal (DMF-DMA), to form Compound 2:

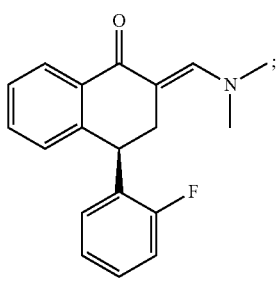
(2)

Step 2: reacting Compound 2:

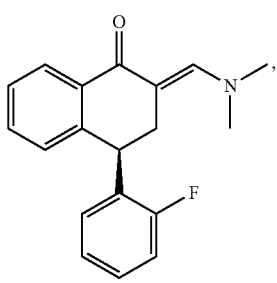
(2)

with Compound 3:

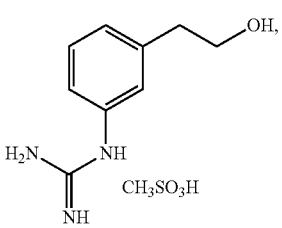
(3)

to form Compound 4:

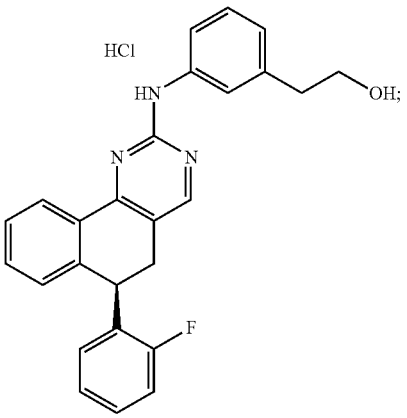
(4)

Step 3: reacting Compound 4:

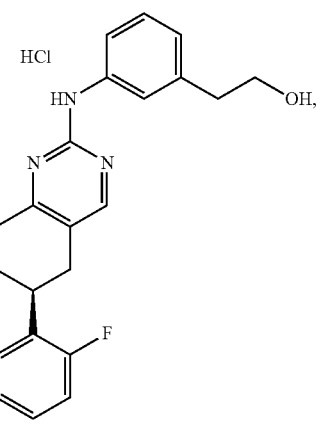
(4)

with methanesulfonyl chloride (MsCl) to form Compound 5:

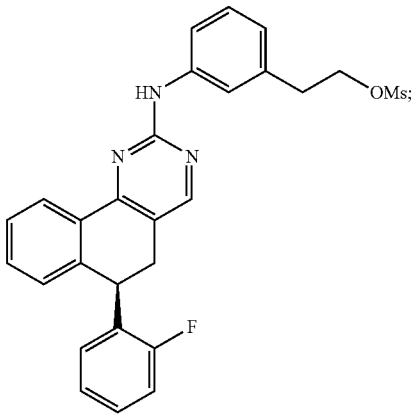
(5)

Step 4: reacting Compound 5:

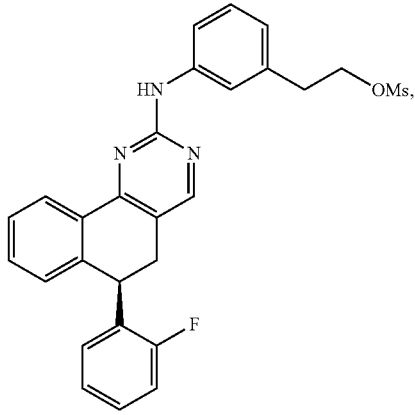

(5)

with methoxyethylamine to form Compound A:

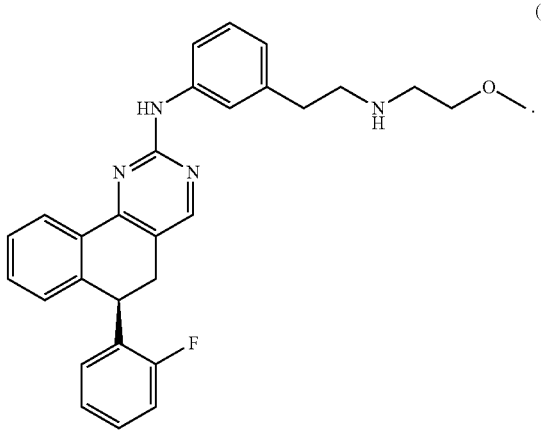

(A)

In one embodiment, the method of the present application comprises Step 1: reacting Compound 1:

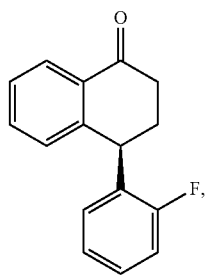

(1)

with N,N-dimethylformamide dimethyl acetal (DMF-DMA), to form Compound 2:

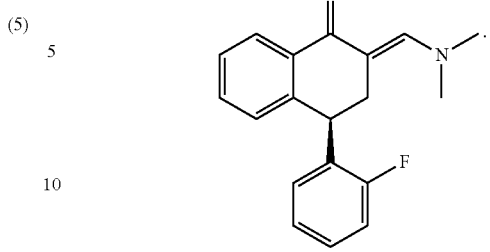

(2)

In one embodiment, Step 1 comprises adding DMF-DMA to Compound 1. In one embodiment, Step 1 comprises reacting Compound 1 with DMF-DMA in the presence of a protic solvent (e.g., an alcohol). In one embodiment, the protic solvent is an alcohol selected from methanol, ethanol, isopropanol, butanol, and t-butanol. In a further embodiment, the alcohol is isopropanol. In one embodiment, Step 1 comprises adding DMF-DMA, together with a protic solvent (e.g., an alcohol, such as isopropanol), to Compound 1.

In one embodiment, Step 1 comprises reacting Compound 1 with DMF-DMA at a temperature below 100° C. In one embodiment, Compound 1 is reacted with DMF-DMA at a temperature between about 60° C. and about 90° C., between about 70° C. and about 90° C., or between about 80° C. and about 85° C.

In one embodiment, Step 1 comprises reacting Compound 1 with DMF-DMA for less than 40 hours. In one embodiment, Compound 1 is reacted with DMF-DMA for less than 36 hours, less than 30 hours, less than 24 hours, or less than 20 hours. In one embodiment, Compound 1 is reacted with DMF-DMA for about 20 hours, about 19 hours, about 18 hours, about 17 hours, about 16 hours, or about 15 hours. In one embodiment, Compound 1 is reacted with DMF-DMA for about 19 hours.

In one embodiment, Step 1 comprises reacting Compound 1 with DMF-DMA at a temperature below 100° C. for less than 40 hours. In a further embodiment, Step 1 comprises reacting Compound 1 with DMF-DMA at a temperature between about 60° C. and about 90° C. for less than 36 hours, less than 30 hours, less than 24 hours, or less than 20 hours. In a further embodiment, Step 1 comprises reacting Compound 1 with DMF-DMA at a temperature between about 80° C. and about 85° C. for less than 20 hours. In a further embodiment, Step 1 comprises reacting Compound 1 with DMF-DMA in the presence of a protic solvent (e.g., an alcohol, such as isopropanol). In a further embodiment, Step 1 comprises adding DMF-DMA, together with a protic solvent (e.g., an alcohol, such as isopropanol), to Compound 1.

In one embodiment, Step 1 may further comprise cooling the reaction between Compound 1 and DMF-DMA (e.g., to a temperature between about 50° C. and about 55° C.).

In one embodiment, Step 1 may further comprise adding a hydrocarbon solvent to the reaction. In one embodiment, the hydrocarbon solvent is $C_6$-$C_{12}$ alkane. In a further embodiment, the hydrocarbon solvent is $C_7$-$C_{12}$ alkane (e.g., $C_7$ alkane, $C_8$ alkane, $C_9$ alkane, $C_{10}$ alkane, $C_{11}$ alkane, or $C_{12}$ alkane). In a further embodiment, the hydrocarbon solvent is n-heptane. In one embodiment, the hydrocarbon solvent (e.g., $C_6$-$C_{12}$ alkane, such as n-heptane) is added after the reaction is cooled. In one embodiment, the hydrocarbon solvent (e.g., $C_6$-$C_{12}$ alkane, such as n-heptane) is added at a temperature between about 50° C. and about 55° C.

In one embodiment, Step 1 may further comprise cooling the reaction between Compound 1 and DMF-DMA (e.g., to a temperature between about 50° C. and about 55° C.), and then adding a hydrocarbon solvent (e.g., $C_6$-$C_{12}$ alkane, such as n-heptane) (e.g., at a temperature between about 50° C. and about 55° C.).

In one embodiment, the addition of a hydrocarbon solvent (e.g., $C_6$-$C_{12}$ alkane, such as n-heptane) generates a slurry. In one embodiment, Step 1 may further comprise, after the addition of the hydrocarbon solvent (e.g., $C_6$-$C_{12}$ alkane, such as n-heptane), stirring the slurry (e.g., at a temperature between about 50° C. and about 55° C.).

In one embodiment, Step 1 may further comprise, after stirring the slurry, adding a hydrocarbon solvent (e.g., $C_6$-$C_{12}$ alkane, such as n-heptane) to the slurry (e.g., at a temperature between about 50° C. and about 55° C.).

In one embodiment, Step 1 may further comprise cooling the slurry. In one embodiment, the cooling comprises: cooling the slurry to a temperature between about 20° C. and about 25° C., and then cooling the slurry to a temperature between about 0° C. and about 5° C. In one embodiment, after cooling the slurry to a temperature between about 20° C. and about 25° C., the slurry is held at a temperature between about 20° C. and about 25° C. for a period between about 15 minutes and about 4 hours (e.g., between 15 minutes and 4 hours, between 15 minutes and 3 hours, between 15 minutes and 2 hours, between 15 minutes and 1.5 hours, between 15 minutes and 1 hour, between 30 minutes and 4 hours, between 30 minutes and 3 hours, between 30 minutes and 2 hours, between 30 minutes and 1.5 hours, or between 30 minutes and 1 hour, or about 1 hour). In one embodiment, after cooling the slurry to a temperature between about 0° C. and about 5° C., the slurry is held at a temperature between about 0° C. and about 5° C. for a period between about 15 minutes and about 4 hours (e.g., between 15 minutes and 4 hours, between 15 minutes and 3 hours, between 15 minutes and 2 hours, between 15 minutes and 1.5 hours, between 15 minutes and 1 hour, between 30 minutes and 4 hours, between 30 minutes and 3 hours, between 30 minutes and 2 hours, between 30 minutes and 1.5 hours, or between 30 minutes and 1 hour, or about 1 hour)).

In one embodiment, Step 1 may further comprise filtering the slurry to produce solid Compound 2.

In one embodiment, Step 1 may further comprise washing Compound 2 (e.g., with a hydrocarbon solvent (e.g., $C_6$-$C_{12}$ alkane, such as n-heptane)) and drying Compound 2.

In one embodiment, Step 1 comprises:

1a. adding DMF-DMA, optionally together with a protic solvent (e.g., an alcohol, such as isopropanol), to Compound 1; and 1b. reacting Compound 1 with DMF-DMA, optionally in the presence of a protic solvent (e.g., an alcohol, such as isopropanol), at a temperature below 100° C. (e.g., between about 80° C. and about 85° C.) for less than 40 hours (e.g., less than 36 hours, less than 30 hours, less than 24 hours, or less than 20 hours).

In one embodiment, Step 1 may further comprise:

1c. cooling the reaction between Compound 1 and DMF-DMA (e.g., to a temperature between about 50° C. and about 55° C.); and 1d. adding a hydrocarbon solvent (e.g., $C_6$-$C_{12}$ alkane, such as n-heptane) to the reaction (e.g., at a temperature between about 50° C. and about 55° C.) to generate a slurry.

In one embodiment, Step 1 may further comprise, in addition to steps 1a, 1b, 1c, and 1d, one or more steps selected from the following:

1e. stirring the slurry from 1d (e.g., at a temperature between about 50° C. and about 55° C.);

1f. adding a hydrocarbon solvent (e.g., $C_6$-$C_{12}$ alkane, such as n-heptane) to the slurry from 1d or 1e (e.g., at a temperature between about 50° C. and about 55° C.);

1g. cooling the slurry from 1d, 1e, or 1f (e.g., to a temperature between about 20° C. and about 25° C.), optionally followed by stirring the slurry (e.g., at a temperature between about 20° C. and about 25° C.);

1h. further cooling the slurry from 1g (e.g., to a temperature between about 0° C. and about 5° C.), optionally followed by stirring the slurry (e.g., at a temperature between about 0° C. and about 5° C.); and 1i. filtering the slurry from 1d, 1e, 1f, 1g, or 1h to produce solid Compound 2.

In one embodiment, the yield of Compound 2 in Step 1 is at least 80%, at least 85%, or at least 87%.

In one embodiment, the method of the present application comprises Step 2: reacting Compound 2:

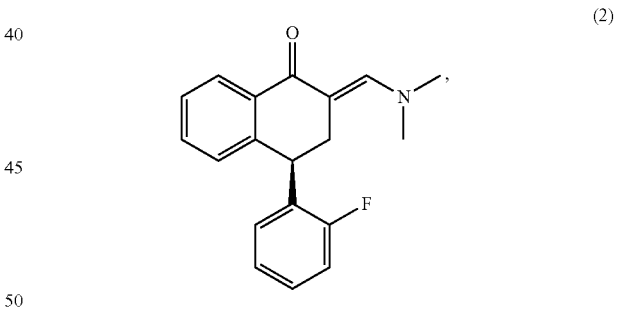

(2)

with Compound 3:

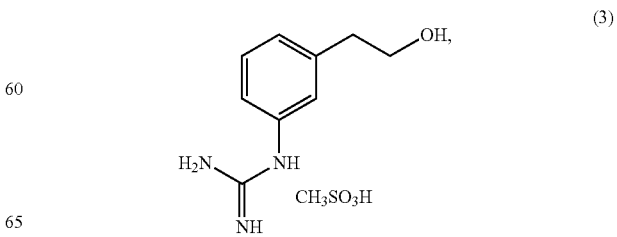

(3)

to form Compound 4:

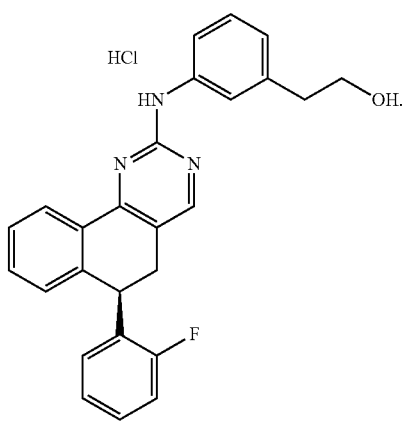

(4)

In one embodiment, Step 2 comprises adding Compound 2 to Compound 3. In one embodiment, Step 1 comprises adding 2-methyltetrahydrofuran (2-MeTHF) and a base (e.g., sodium ethoxide in ethanol) to Compound 3, and then adding Compound 2. In one embodiment, the mixture of Compound 3, 2-MeTHF, and the base is stirred at a temperature between about 20° C. and about 25° C. for a period between about 15 minutes and about 4 hours (e.g., between 30 minutes and 4 hours, between 30 minutes and 3 hours, between 30 minutes and 2.5 hours, between 1 hour and 4 hours, between 1 hour and 3 hours, between 1 hour and 2.5 hours, between 1.5 hours and 4 hours, between 1.5 hours and 3 hours, or between 1.5 hours and 2.5 hours, or about 2 hours), before Compound 2 is added.

In one embodiment, Step 2 comprises reacting Compound 2 with Compound 3 at a temperature between about 75° C. and about 80° C. for between about 24 hours and about 48 hours (e.g., about 24 hours, about 30 hours, about 36 hours, about 42 hours, or about 48 hours).

In one embodiment, Step 2 may further comprise cooling the reaction mixture between Compound 2 and Compound 3 (e.g., to a temperature between about 20° C. and about 25° C.). In one embodiment, the reaction mixture is optionally washed with a NaCl solution (e.g., 3% NaCl) after the cooling.

In one embodiment, Step 2 may further comprise distilling the organic phase generated in the reaction between Compound 2 and Compound 3. In one embodiment, Step 2 may further comprise, after the distillation, adding 2-MeTHF to the organic phase and distilling further (e.g., to achieve a water content of no greater than 0.5%) to generate a dried 2-MeTHF solution. In one embodiment, Step 2 may further comprise adding 2-MeTHF to and filtering the dried 2-MeTHF solution.

In one embodiment, Step 2 may further comprise adding water to the dried 2-MeTHF solution, and heating the solution (e.g., to a temperature between about 60° C. and about 65° C.).

In one embodiment, Step 2 may further comprise adding HCl after the reaction between Compound 2 and Compound 3. In one embodiment, HCl is in a solution of 2-MeTHF before being added. In one embodiment, HCl is added at a temperature between about 60° C. and about 65° C. In one embodiment, HCl is added gradually (e.g., over a period of about 30 minutes).

In one embodiment, Step 2 may further comprise adding a seed Compound 4 after the addition of HCl to generate a slurry. In one embodiment, the slurry is stirred (e.g. for about 1 hour). In one embodiment, HCl is added to the slurry. In one embodiment, HCl is in a solution of 2-MeTHF before being added to the slurry. In one embodiment, HCl is added gradually (e.g., over a period of about 1.5 hours). In one embodiment, the slurry is further stirred after the addition of HCl (e.g., at a temperature between about 60° C. and about 65° C. for about 1 hour).

In one embodiment, Step 2 may further comprise cooling the slurry (e.g., to a temperature between about 20° C. and about 25° C.). In one embodiment, the slurry is cooled gradually (e.g., over a period of about 2 hours). In one embodiment, the slurry is stirred. In one embodiment, the slurry is stirred at a temperature between about 20° C. and about 25° C. (e.g., for a period between about 12 hours and about 24 hours (e.g., for about 16 hours)).

In one embodiment, Step 2 may further comprise filtering the slurry to produce solid Compound 4.

In one embodiment, Step 2 may further comprise washing Compound 4 (e.g., with 2-MeTHF) and drying Compound 4.

In one embodiment, Step 2 comprises:

2a. adding Compound 2 to Compound 3, optionally preceded by the addition of 2-MeTHF and a base (e.g., sodium ethoxide in ethanol) to Compound 3;

2b. reacting Compound 2 and Compound 3 at a temperature between about 75° C. and about 80° C. for between about 24 hours and about 48 hours;

2c. adding HCl after the reaction between Compound 2 and Compound 3 (e.g., at a temperature between about 60° C. and about 65° C.); and 2d. optionally adding a seed Compound 4 to generate a slurry.

In one embodiment, Step 2 may further comprise, after 2b and before 2c, one or more steps selected from the following:

2ab1. cooling the reaction between Compound 2 and Compound 3 (e.g., to a temperature between about 20° C. and about 25° C.), and optionally washing the reaction with a NaCl solution after the cooling;

2ab2. distilling the organic phase generated in the reaction between Compound 2 and Compound 3;

2ab3. adding 2-MeTHF to the organic phase and distilling further (e.g., to achieve a water content of no greater than 0.5%) to generate a dried 2-MeTHF solution; and 2ab4. adding water to the dried 2-MeTHF solution, and optionally heating the solution (e.g., to a temperature between about 60° C. and about 65° C.).

In one embodiment, Step 2 may further comprise, after 2d, one or more steps selected from the following:

2e. stirring the slurry from 2d;

2f. adding HCl (e.g. in a solution of 2-MeTHF) to the slurry from 2d or 2e;

2g. cooling the slurry from 2d, 2e, or 2f (e.g., to a temperature between about 20° C. and about 25° C.);

2h. stirring the slurry from 2g (e.g., at a temperature between about 20° C. and about 25° C.); and 2i. filtering the slurry from 2d, 2e, 2f, 2g, or 2h to produce solid Compound 4.

In one embodiment, the yield of Compound 3 in Step 2 is at least 70%, at least 75%, or at least 80%.

In one embodiment, the method of the present application comprises Step 3: reacting Compound 4:

(4)

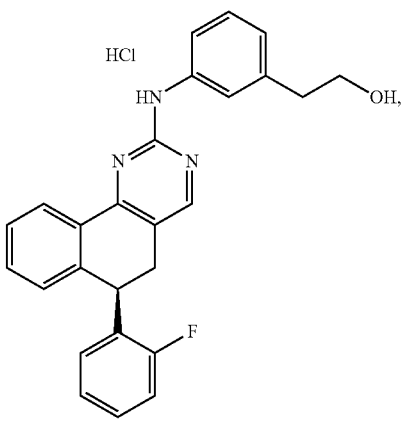

with methanesulfonyl chloride (MsCl) to form Compound 5:

(5)

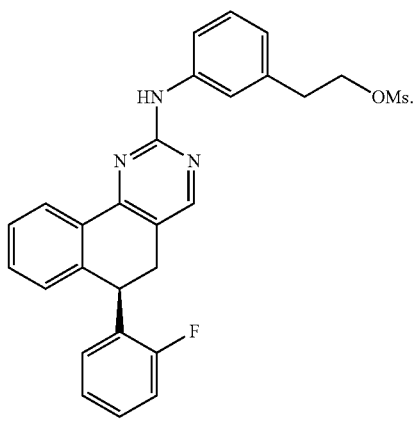

In one embodiment, Step 3 comprises treating Compound 4 with a base (e.g., NaOH), optionally preceded by forming a Compound 4 slurry in 2-MeTHF. In one embodiment, Step 3 comprises adding a base (e.g., NaOH) to Compound 4 (e.g., the Compound 4 slurry in 2-MeTHF) and stirring the resulting mixture (e.g., at a temperature between about 20° C. and about 25° C.).

In one embodiment, Step 3 may further comprise, after the stirring, removing the aqueous phase and keeping the organic phase. In one embodiment, Step 3 may further comprise washing the organic phase (e.g., with a NaCl solution).

In one embodiment, Step 3 may further comprise concentrating the organic phase. In one embodiment, Step 3 may further comprise adding 2-MeTHF to the organic phase and distilling further (e.g., to achieve a water content of no greater than 0.1%).

In one embodiment, Step 3 comprises, after treating Compound 4 with a base, adding triethylamine to the mixture, and optionally cooling the mixture (e.g., to a temperature between about 0° C. and about 5° C.).

In one embodiment, Step 3 comprises, after the addition of triethylamine, adding MsCl to the mixture gradually (e.g., over a period of about 1 hour). In one embodiment, during the addition of MsCl, the temperature of the mixture is kept no greater than about 20° C. In one embodiment, after addition of MsCl, the mixture is heated (e.g., to a temperature between about 20° C. and about 25° C.). In one embodiment, after addition of MsCl, the mixture is stirred (e.g., at a temperature between about 20° C. and about 25° C.). In one embodiment, after addition of MsCl, the mixture is stirred (e.g., for about 2 hours).

In one embodiment, Step 3 may further comprise, after the reaction between Compound 4 and MsCl, adding additional triethylamine and MsCl to the mixture, for once, twice, or more times. In one embodiment, after each additional addition of triethylamine and MsCl, the mixture is stirred (e.g., at a temperature between about 20° C. and about 25° C.) for between about 1 hour and about 4 hours (e.g., about 1.5 hours).

In one embodiment, Step 3 may further comprise, after the reaction between Compound 4 and MsCl, adding water to the reaction mixture, and optionally stirring the mixture (e.g., for about 2.5 hours) and settling the mixture to form a biphasic mixture. In one embodiment, the aqueous phase is collected and extracted with 2-MeTHF. In one embodiment, after the extraction, the organic phase is collected, and optionally washed (e.g., with NaCl solution) and concentrated. In one embodiment, additional 2-MeTHF is added to the organic phase and the organic phase is distilled further (e.g., reduce the water content (e.g., to no greater than 0.1%)).

In one embodiment, Step 3 comprises:

3a. adding a base (e.g., NaOH) to Compound 4, optionally preceded by forming a Compound 4 slurry in 2-MeTHF;

3b. adding triethylamine, and optionally cooling the mixture (e.g., to a temperature between about 0° C. and about 5° C.); and 3c. adding MsCl, and optionally heating the mixture (e.g., to a temperature between about 20° C. and about 25° C.).

In one embodiment, Step 3 may further comprise, after 3a and before 3b, one or more steps selected from the following:

3ab1. after adding the base (e.g., NaOH) to Compound 4, stirring the resulting mixture (e.g., at a temperature between about 20° C. and about 25° C.);

3ab2. after the stirring, removing the aqueous phase and keeping the organic phase; and 3ab3. concentrating the organic phase, and adding 2-MeTHF to the organic phase and distilling the organic phase.

In one embodiment, Step 3 may further comprise, after 3c, one or more steps selected from the following:

3d. adding additional triethylamine and MsCl to the mixture, for once, twice, or more times, and after each additional addition of triethylamine and MsCl, optionally stirring the mixture (e.g., at a temperature between about 20° C. and about 25° C.) for between about 1 hour and about 4 hours (e.g., about 1.5 hours);

3e. after the reaction between Compound 4 and MsCl, adding water to the reaction mixture, optionally stirring the mixture (e.g., for about 2.5 hours), and collecting the aqueous phase; and 3f. extracting the aqueous phase with 2-MeTHF, and collecting the organic phase.

In one embodiment, the method of the present application comprises Step 4: reacting Compound 5:

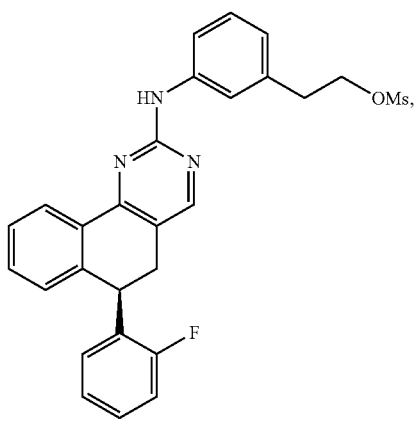

(5)

with methoxyethylamine to form Compound A:

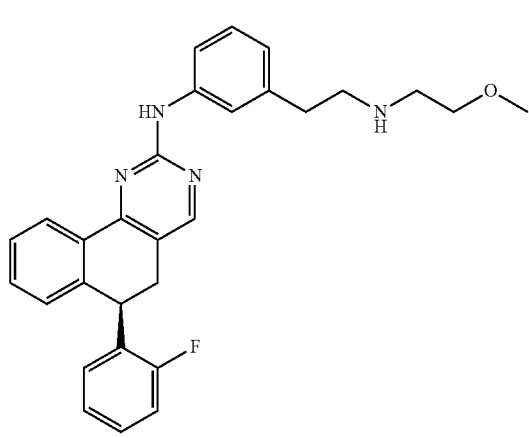

(A)

In one embodiment, Step 4 comprises adding methoxyethylamine to Compound 5 and heating the mixture (e.g., to a temperature below 90° C. (e.g., between about 40° C. and about 70° C., between about 50° C. and about 60° C., or between about 50° C. and about 55° C.)). In one embodiment, the mixture is stirred (e.g., for between about 10 hours and about 18 hours, between about 12 hours and about 15 hours, or about 13 hours).

In one embodiment, Step 4 may further comprise, after the reaction between Compound 5 and methoxyethylamine, adding a solvent (e.g., isopropylacetate, 2-MeTHF, or dichlormethane) and water to the reaction mixture (e.g., at a temperature below 90° C. (e.g., between about 40° C. and about 70° C., between about 50° C. and about 60° C., or between about 50° C. and about 55° C.)). In one embodiment, the solvent is isopropylacetate. In one embodiment, after addition of the isopropylacetate and water, the mixture is stirred and settled to form a biphasic mixture. In one embodiment, the aqueous phase is collected and extracted with a solvent (e.g., isopropylacetate, 2-MeTHF, or dichlormethane). In one embodiment, the solvent is isopropylacetate. In one embodiment, after the extraction, the organic phase is collected, optionally washed (e.g., with water), and distilled to form a slurry. In one embodiment, a solvent that allows the removal of isopropylacetate through distillation is added to the slurry. In one embodiment, the solvent is a non-polar hydrocarbon solvent that has a boiling point higher than isopropylacetate. In one embodiment, the non-polar hydrocarbon solvent is a $C_7$-$C_{12}$ alkane (e.g., $C_7$ alkane, $C_8$ alkane, $C_9$ alkane, $C_{10}$ alkane, $C_{11}$ alkane, or $C_{12}$ alkane). In one embodiment, the non-polar hydrocarbon solvent is n-heptane. In one embodiment, after the addition of the solvent (e.g., a $C_7$-$C_{12}$ alkane, such as n-heptane), the slurry is stirred (e.g., at a temperature between about 20° C. and about 25° C.). In one embodiment, the slurry is stirred for about 16 hours.

In one embodiment, Step 4 may further comprise filtering the slurry to produce solid Compound A.

In one embodiment, Step 4 may further comprise washing Compound A (e.g., with a non-polar hydrocarbon solvent, such as $C_7$-$C_{12}$ alkane (e.g., $C_7$ alkane, $C_8$ alkane, $C_9$ alkane, $C_{10}$ alkane, $C_{11}$ alkane, or $C_{12}$ alkane)) and dried Compound A (e.g., at a temperature between about 40° C. and about 45° C.).

In one embodiment, the yield of Compound A in Step 4 is at least 75%, at least 80%, or at least 85%.

The present application also provides methods of making a polymorph of Compound A dihydrochloride salt:

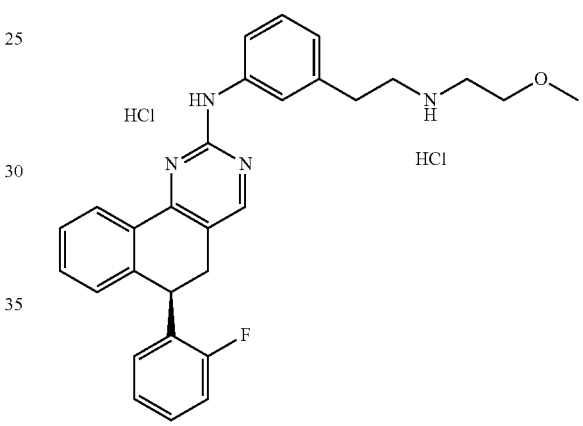

comprising Step 5a: reacting Compound A:

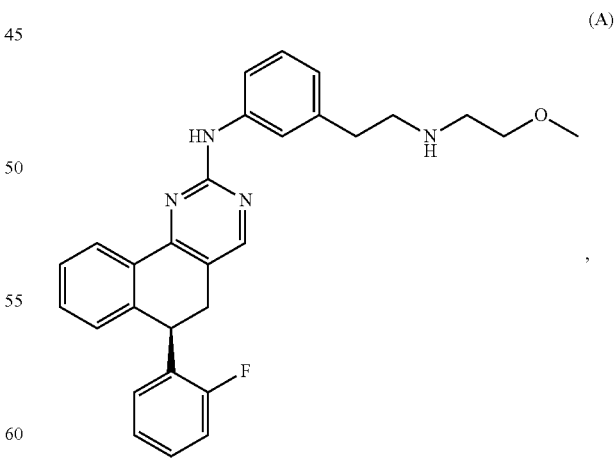

(A)

with HCl.

In one embodiment, Compound A is prepared by the methods described herein.

In one embodiment, Step 5a comprises adding HCl to a solution of Compound A, optionally preceded by dissolving Compound A in acetone (e.g., at a temperature between about 50° C. and about 55° C.). In one embodiment, HCl is added to the Compound A solution at a temperature between about 50° C. and about 55° C. In one embodiment, HCl is added to the Compound A solution gradually (e.g., over a period of about 60 minutes). In one embodiment, Compound A is reacted with HCl at a temperature between about 50° C. and about 55° C.

In one embodiment, Step 5a may further comprise adding acetone (e.g., at a temperature between about 50° C. and about 55° C.), after the reaction between Compound A and HCl. In one embodiment, the acetone is added gradually (e.g., over a period of about 1.75 hours).

In one embodiment, Step 5a may further comprise adding a seed polymorph of Compound A dihydrochloride salt, after the reaction between Compound A and HCl, to form a slurry.

In one embodiment, Step 5a may further comprise adding acetone (e.g., at a temperature between about 50° C. and about 55° C.) to the slurry. In one embodiment, the acetone is added gradually (e.g., over a period of about 4.25 hours).

In one embodiment, Step 5a may further comprise cooling the slurry (e.g., to a temperature between about 20° C. and about 25° C.). In one embodiment, the slurry is cooled gradually (e.g., over a period of about 2.5 hours).

In one embodiment, Step 5a may further comprise stirring the slurry (e.g., at a temperature between about 20° C. and about 25° C.). In one embodiment, the slurry is stirred for about 4.5 hours.

In one embodiment, Step 5a further comprises filtering and drying the slurry to produce a polymorph of Compound A dihydrochloride salt.

In one embodiment, the method of making a polymorph of Compound A dihydrochloride salt may further comprise, after Step 5a, Step 5b: recrystallizing the polymorph of Compound A dihydrochloride salt.

In one embodiment, Step 5b comprises mixing the polymorph of Compound A dihydrochloride salt with acetone and water; and heating the mixture. In one embodiment, the mixture is heated to a temperature between about 40° C. and about 55° C. (e.g., between about 45° C. and about 52° C., or about 50° C.).

In one embodiment, Step 5b may further comprise adding acetone to the mixture, optionally preceded by filtering and heating the mixture. In one embodiment, the mixture is heated (e.g., to above 50° C. (e.g., about 55° C.)). In one embodiment, after the addition of acetone, the mixture is cooled (e.g., to below 55° C. (e.g., about 50° C.)).

In one embodiment, Step 5b may further comprise adding a seed polymorph of Compound A dihydrochloride salt to generate a slurry.

In one embodiment, Step 5b may further comprise stirring the slurry (e.g., at about 50° C.). In one embodiment, the slurry is stirred for about 30 minutes. In one embodiment, the slurry is cooled after the stirring (e.g., to about 20° C.).

In one embodiment, Step 5b may further comprise heating the slurry (e.g., from about 20° C. to about 40° C.), and adding acetone (e.g., at about 40° C.). In one embodiment, the slurry is cooled after the addition of acetone (e.g., from about 40° C. to about 20° C.). In one embodiment, the slurry is stirred after the cooling (e.g., at about 20° C.). In one embodiment, the slurry is stirred for between about 12 hours and about 24 hours (e.g., about 12 hours, about 16 hours, about 20 hours, or about 24 hours).

In one embodiment, Step 5b may further comprise washing the slurry (e.g., with acetone) and filtering the slurry to produce a polymorph of Compound A dihydrochloride salt.

In one embodiment, the polymorph of Compound A dihydrochloride salt is characterized by an X-ray powder diffraction pattern comprising peaks at approximately 14.9, 23.1, and 23.8° 2θ using Cu Kα radiation. In one embodiment, the polymorph of Compound A dihydrochloride salt is characterized by an X-ray powder diffraction pattern comprising peaks at approximately 10.6, 14.9, 23.1, 23.8, and 24.8° 2θ using Cu Kα radiation. In one embodiment, the polymorph of Compound A dihydrochloride salt is characterized by an X-ray powder diffraction pattern comprising peaks at approximately 10.6, 13.9, 14.9, 21.8, 22.3, 23.1, 23.8, 24.8, 28.1, and 28.7° 2θ using Cu Kα radiation. In one embodiment, the polymorph of Compound A dihydrochloride salt is characterized by an X-ray powder diffraction pattern comprising peaks at approximately 10.6, 11.6, 13.9, 14.9, 19.0, 21.8, 22.3, 23.1, 23.8, 24.8, 25.3, 28.1, 28.2, and 28.7° 2θ using Cu Kα radiation. In one embodiment, the polymorph of Compound A dihydrochloride salt is characterized by an X-ray powder diffraction pattern substantially similar to that set forth in FIG. 1.

In one embodiment, the method of the present application is shown in Scheme I below:

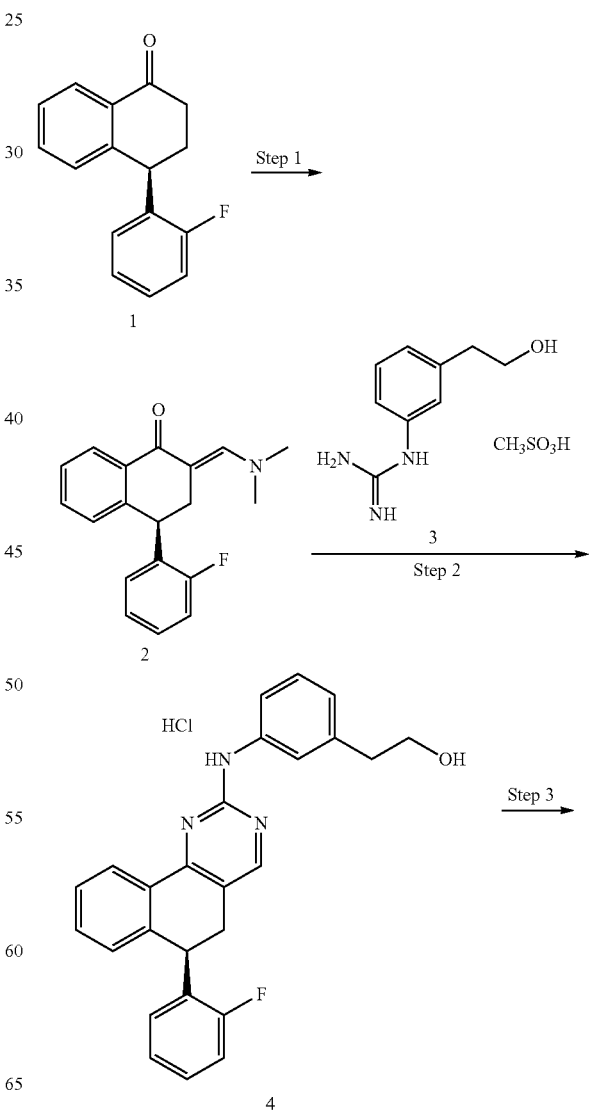

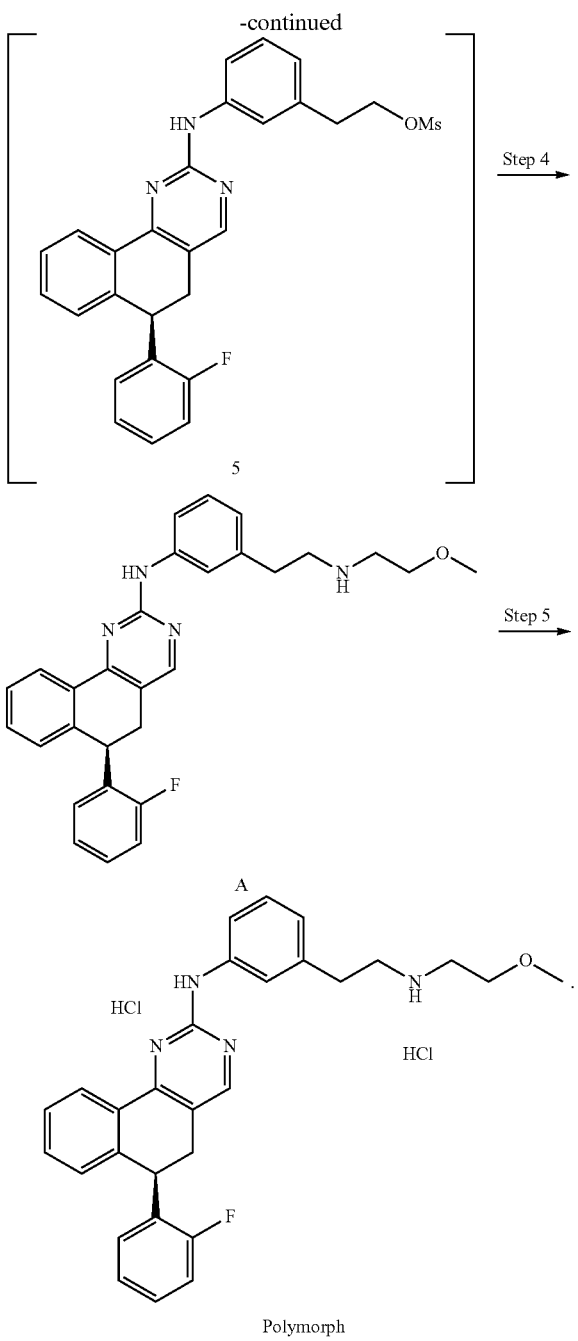

In one embodiment, the methods of the present application produce Compound A or a salt thereof or a polymorph of Compound A dihydrochloride salt at at least 50%, at least 55%, at least 60%, at least 65%, at least 70%, at least 75%, at least 80%, at least 85%, at least 90%, or at least 95% yield. In one embodiment, the methods of the present application produce Compound A or a salt thereof or a polymorph of Compound A dihydrochloride salt at at least 60%, at least 65%, at least 70%, at least 75%, at least 80%, at least 85%, at least 90%, or at least 95% yield.

In one embodiment, the methods of the present application produce substantially pure Compound A or a salt thereof or a polymorph of Compound A dihydrochloride salt. The term "purity" as used herein refers to the amount of Compound A or a salt thereof or a polymorph of Compound A dihydrochloride salt based on analytic methods commonly used in the art (e.g., HPLC). Purity is based on the "organic" purity of the compound, and does not include a measure of any amount of water, solvent, etc. In one embodiment, the purity of Compound A or a salt thereof or a polymorph of Compound A dihydrochloride salt is compared to the purity of a reference standard, e.g. a known sample of Compound A by comparing the area under the peak in HPLC. In one embodiment, Compound A or a salt thereof or a polymorph of Compound A dihydrochloride salt prepared according to the methods of the present application has a purity of greater than about 96%. In one embodiment, Compound A or a salt thereof or a polymorph of Compound A dihydrochloride salt prepared according to the methods of the present application has a purity of greater than about 98%. For example, the purity of Compound A or a salt thereof or a polymorph of Compound A dihydrochloride salt prepared according to the methods of the present application is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of Compound A or a salt thereof or a polymorph of Compound A dihydrochloride salt prepared according to the methods of the present application is 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of Compound A or a salt thereof or a polymorph of Compound A dihydrochloride salt prepared according to the methods of the present application is 98.0%, 98.5%, 99.0%, 99.5%, 99.6%, 99.7%, 99.8%, or 99.9%.

In one embodiment, the methods of the present application produce highly pure Compound A or a salt thereof or a polymorph of Compound A dihydrochloride salt on a large scale (e.g., commercial scale). The term "commercial scale" refers to yield of a single batch of at least about 100 g. In one embodiment, the methods of the present application produce highly pure Compound A or a salt thereof or a polymorph of Compound A dihydrochloride salt in a large amount of at least 100 g, at least 200 g, at least 500 g, at least 1 kg, at least 2 kg, or at least 5 kg.

Characterization Methods and Assays $^1$H Nuclear Magnetic Resonance ($^1$H NMR)

$^1$H-NMR experiments were performed on a Bruker AV400 (frequency: 400 MHz). Experiments were performed in an appropriate solvent and each sample was prepared to ca. 10 mM concentration.

Ion Chromatography 10 mg samples were weighed, diluted in 5 mL water (or water:methanol {4%}) and then analyzed for chloride content using the following experimental conditions:

Instrument: Dionex Chromatography System
Column: Dionex IonPac AS14A-5 μm, 3×150 mm
Guard Column: Dionex IonPac AG14A-5 μm, 3×30 mm
Mobile Phase: 15 mM Potassium Hydroxide
Flow Rate: 0.6 mL/min
Runtime: 25 minutes
Detector suppression: 50 mA, water regenerant as required
Column Temperature: 30° C.
Injection Volume: 25 μL High Performance Liquid Chromatography-Ultraviolet Detection (HPLC-UV)

Purity was determined by first diluting samples in acetonitrile:water (50%) to 100 mg/mL; solubility was determined by diluting 100 µL saturated solution in 900 µL acetonitrile: water (50%). Samples were then analyzed using the following experimental conditions:

Setting 1:
  Instrument: Agilent 1100
  Column: Phenomenex Luna C18 5µ 150×4.6 mm LC/031
  Column Temperature: 25° C.
  Autosampler Temperature: 20° C.
  UV wavelength: 255 nm
  Injection Volume: 5 µL
  Flow Rate: 1 mL/min
  Mobile Phase A: 0.1% TFA
  Mobile Phase B: 0.085% TFA in Acetonitrile
  Gradient program:

| Time (minutes) | Solvent B [%] |
|---|---|
| 0 | 5 |
| 45 | 95 |
| 55 | 95 |
| 55.1 | 5 |
| 60 | 5 |

Setting 2:
  Instrument: Agilent 1100
  Column: Phenomenex Luna C18 5µ 150×4.6 mm LC/031
  Column Temperature: 25° C.
  Autosampler Temperature: Ambient
  UV wavelength: 280 nm
  Injection Volume: 5 µL
  Flow Rate: 1 mL/min
  Mobile Phase A: 95:5:01% v/v/v/$H_2O$:Methanol:TFA
  Mobile Phase B: 95:5:01% v/v/v/Methanol:$H_2O$:TFA
  Gradient program:

| Time (minutes) | Solvent A [%] | Solvent B [%] |
|---|---|---|
| 0.0 | 90 | 10 |
| 8.0 | 65 | 35 |
| 10.0 | 30 | 70 |
| 24.0 | 20 | 80 |
| 30.0 | 5 | 95 |
| 35.0 | 0 | 100 |
| 35.1 | 90 | 10 |
| 40.0 | 90 | 10 |

Biological Assays

The present application provides methods to assess biological activities of the compounds of the application. In one method, an assay based on enzymatic activity can be utilized. In one specific enzymatic activity assay, the enzymatic activity is from a kinase (e.g., FGFR). As used herein, "kinase" refers to enzymes which catalyze the transfer of the γ-phosphate from ATP to the hydroxyl group on the side chain of Ser/Thr or Tyr in proteins and peptides and are intimately involved in the control of various important cell functions, such as signal transduction, differentiation, and proliferation. Preferably, the kinase assayed is a tyrosine kinase (e.g., FGFR).

A change in enzymatic activity caused by compounds of the present application can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules, and plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. Specific methods for assessing the biological activity of the disclosed compounds are described in the examples.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., Molecular Cloning, *A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., $18^{th}$ edition (1990). These texts can, of course, also be referred to in making or using an aspect of the disclosure Pharmaceutical Compositions The present disclosure also provides pharmaceutical compositions comprising Compound A or a salt thereof or a polymorph of Compound A dihydrochloride salt prepared by the methods of the present application, in combination with at least one pharmaceutically acceptable excipient or carrier.

A "pharmaceutical composition" is a formulation containing the compounds of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of Compound A or a salt thereof or a polymorph of Compound A dihydrochloride salt) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the present disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the present application can be administered to a subject in many of the well-known methods currently used for chemotherapeutic treatment. For example, for treatment of cancers, a compound of the present application may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present application are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound employed. An ordinarily skilled physician or veterinarian can readily determine and prescribe the effective amount of the drug required to prevent, counter or arrest the progress of the condition.

Techniques for formulation and administration of the disclosed compounds of the disclosure can be found in *Remington: the Science and Practice of Pharmacy,* 19$^{th}$ edition, Mack Publishing Co., Easton, Pa. (1995). In an embodiment, the compounds described herein are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

Methods of Treatment

The present application provides methods for the treatment of a cell proliferative disorder in a subject in need thereof by administering to the subject a therapeutically effective amount of Compound A or a salt thereof or a polymorph of Compound A dihydrochloride salt prepared by the methods of the present application. The present application also provides methods of protecting against a cell proliferative disorder in a subject in need thereof by administering to the subject a therapeutically effective amount of Compound A or a salt thereof or a polymorph of Compound A dihydrochloride salt prepared by the methods of the present application. The cell proliferative disorder can be cancer or a precancerous condition. The present application further provides the use of Compound A or a salt thereof or a polymorph of Compound A dihydrochloride salt prepared by the methods of the present application for the preparation of a medicament useful for the treatment or prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue.

A cell proliferative disorder includes a precancer or a precancerous condition. A cell proliferative disorder includes cancer. Preferably, the methods provided herein are used to treat or alleviate a symptom of cancer.

The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

As used herein, "treating" or "treat" describes the management and care of a patient for the purpose of combating a disease, condition, or disorder and includes the administration of a compound of the present disclosure to alleviate the symptoms or complications of a disease, condition or disorder, or to eliminate the disease, condition or disorder.

As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the present application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein the term "symptom" is defined as an indication of disease, illness, injury, or that something is not right in the body. Symptoms are felt or noticed by the individual experiencing the symptom, but may not easily be noticed by others.

As used herein the term "sign" is also defined as an indication that something is not right in the body. But signs are defined as things that can be seen by a doctor, nurse, or other health care professional.

EXAMPLES

Example 1. Preparation of Compound 2

Starting materials: (R)-4-(2-fluorophenyl)-3,4-dihydronaphthalen-1(2H)-one (Compound 1)
Reagents: N,N-Dimethylformamide dimethyl acetal (DMF-DMA)
Solvents: Isopropyl alcohol (iPrOH)
n-Heptane A 50-gallon reactor was charged with Compound 1 (8.0 kg, 33.3 mol, 1.0 eq) followed by of isopropyl alcohol (iPrOH, 19.2 kg, 24.5 L, 3 vol) and N,N-dimethylformamide dimethyl acetal (DMF-DMA, 15.8 kg, 133.2 mol, 4.0 eq). The batch was heated to reflux (80-85° C.) for 19 hours. The reaction was cooled to 50-55° C. and n-heptane (54.9 kg, 80.2 L, 10 vol) was added while maintaining a temperature of 50-55° C. Once the addition of n-heptane was complete, the resulting slurry was transferred to a 100-gallon reactor and stirred at 50-55° C. Additional n-heptane (54.9 kg, 80.2 L, 10 vol) was added to the 100-gallon reactor while maintaining an internal temperature of 50-55° C. The mixture was then cooled to 20-25° C. and held for one hour before cooling further to 0-5° C. After a one hour hold, the slurry was filtered and the wet cake was washed with cold (0-5° C.) n-heptane (218 kg, 31.8 L, 8 vol). The solid was dried under vacuum at 20-25° C. for 19 h to afford Compound 2 (8.5 kg, 87% yield, 98.4% AUC) as a yellow solid.

Example 2. Preparation of Compound 4

Starting materials: (R)-2-((dimethylamino)methylene)-4-(2-fluorophenyl)-3,4-dihydronaphthalen-1(2H)-one (Compound 2)
1-(3-(2-hydroxyethyl)phenyl)guanidine methanesulfonate (Compound 3)
Reagents: 36% Hydrochloric Acid (HCl)
Sodium Chloride (NaCl)
21% Sodium Ethoxide in Ethanol (NaOEt/EtOH)
Solvents: 2-Methyl Tetrahydrofuran (2-MeTHF)

A 100-gallon reactor was charged with Compound 3 (8.4 kg, 30.6 mol, 1.06 eq) followed by 2-methyltetrahydrofuran (2-MeTHF, 93.8 kg, 109.8 L, 13 vol) and 21% sodium ethoxide in ethanol (9.8 kg, 11.3 L, 1.06 eq). The mixture was stirred at 20-25° C. for two hours before Compound 2 (8.5 kg, 28.8 mol, 1.0 eq) was added. The reaction was then heated to reflux (75-80° C.) for 36 hours until the target specification for reaction completion was achieved. The reaction mixture was cooled to 20-25° C. and washed with 3% NaCl (3×42 L, 3×5 vol). The organic layer was vacuum distilled to 85 L (10 vol) and chased five times with 2-MeTHF (36.2 kg, 42.4 L, 5 vol) to achieve the desired water content of ≤0.5% (0.52%). The dried 2-MeTHF solution (85 L, 10 vol) was diluted with additional 2-MeTHF (72.7 kg, 85.1 L, 10 vol) and polish filtered. Water (0.8 kg) was added to prepare a 1% v/v solution of water in 2-MeTHF and the mixture was heated to 60-65° C. A 0.5 M solution of HCl in 2-MeTHF (20.8 L, 10.4 mol, 0.36 eq) was added over a period of 0.5 h while maintaining a temperature of 60-65° C. The resulting solution was seeded with Compound 4 seeds (85g, 1 wt %) and stirred for 1 hour before additional 0.5 M solution of HCl in 2-MeTHF (41.5 L, 21.2 mol, 0.74 eq) was added over a period of 1.4h. After stirring for 1 hour at 60-65° C., the slurry was cooled to 20-25° C. over a period of 2 hours and then stirred at 20-25° C. for an additional 16 hours. The slurry was filtered and the wet cake was washed twice with 2-MeTHF (29.0 kg, 34 L, 4 vol). The solid was dried under vacuum at 45° C. for 17.5 h to afford Compound 4 (10.4 kg, 81%, 99.4% AUC) as a yellow solid.

Example 3. Preparation of Compound 5 and Compound A

Starting material: Compound 4
Methanesulfonyl chloride (MSCl) [CAS 124-63-0]
2-Methoxyethylamine [CAS 109-85-3]
Reagents: Sodium Chloride (NaCl)
50% Sodium Hydroxide (NaOH)
Triethylamine (Et$_3$N)
Solvents: n-Heptane
Isopropyl Acetate (iPrOAc)
2-Methyl Tetrahydrofuran (2-MeTHF)

A 100-gallon reactor was charged with Compound 4 (10.4 kg, 23.2 mol, 1.0 eq) and 2-methyltetrahydrofuran (2-MeTHF, 132.6 kg, 155.2 L, 15 vol). A solution of 1.0 M NaOH (48.5 L, 48.5 mol, 2.1 eq) was added in one portion to the slurry and the resulting biphasic mixture was allowed to stir at 20-25° C. for 1.0 h. The phases were allowed to settle, the lower aqueous layer was removed and the organic layer was washed with 2.5% NaCl (52 L, 5 vol). The organic layer was concentrated down to 104 L (10 vol) and chased with 2-MeTHF (44.0 kg, 51.5 L, 5 vol) a total of five times to achieve the desired water content of ≤0.1% (0.08%). After polish-filtering the 2-MeTHF solution into a clean 100-gallon reactor, triethylamine (Et$_3$N, 3.5 kg, 4.9 L, 34.8 mol, 1.5 eq) was added and the mixture was cooled to 0-5° C. Methanesulfonyl chloride (MsCl, 4.0 kg, 2.7 L, 34.8 mol, 1.5 eq) was added over a period of 1 h while keeping the internal temperature ≤20° C. Once the addition of MSCl was complete, the reaction temperature was adjusted to 20-25° C. and the mixture was stirred for 2 h. Analysis by HPLC indicated the presence of 3.7% Compound 4. Additional Et₃N (0.4 kg, mL, 0.55 L, 4.0 mol, 0.2 eq) and MSCl (0.4 kg, 0.27 L, 3.5 mol, 0.15 eq) were charged and the mixture was stirred at 20-25° C. for 1.5 h. At this point, 0.57% Compound 4 was detected by HPLC. Additional Et₃N (0.1 kg, mL, 0.14 L, 1.0 mol, 0.05 eq) and MSCl (0.1 kg, 0.07 L, 1.0 mol, 0.05 eq) were charged and the mixture was stirred at 20-25° C. for 1.5 h. Water (93.5 kg, 9 vol) was added and the biphasic mixture was stirred for 2.5 h. The phases were allowed to settle for 1 h and the aqueous layer was then transferred to a clean 200-gallon reactor. The aqueous layer was back-extracted with 2-MeTHF (44.6 kg, 52.2 L, 5 vol) and the upper layer was transferred to the 100-gallon reactor to combine organic layers before being washed with 5% NaCl (51.6 kg, 5 vol). The resulting 2-MeTHF solution was concentrated down to ~104 L (10 vol) and then chased with 2-MeTHF (44.0 kg, 51.5 L, 5 vol) a total of five times to achieve the desired water content of ≤0.1% (0.02%). After polish-filtering the 2-MeTHF solution into a clean 100-gallon reactor, the solution containing Compound 5 was concentrated down to 52 L (5 vol). 2-methoxyethylamine (35.8 kg, 41.4 L, 4 vol) was added, and the resulting reaction mixture was heated to 50-55° C. The reaction mixture was allowed to stir at temperature for 13 h and HPLC analysis indicated complete conversion. Once the transformation was deemed complete, isopropylacetate (iPrOAc, 117.8 kg, 135 L, 13 vol) and water (104 kg, 10 vol) were charged to the reactor while maintaining a temperature of 50-55° C. After stirring for 1.5 h, the water layer was transferred to a clean 200-gallon reactor and extracted with iPrOAc (61.8 kg, 70.9 L, 7 vol). The upper layer was transferred to the 100-gallon reactor to combine organic layers and then re-equilibrated at 50-55° C. The combined organic layer was washed with water (4×20.8 kg, 4×2 vol) before being vacuum distilled down to 63 L (6 vol). The resulting slurry was chased with n-heptane (3×85.0 kg, 3×124 L, 3×12 vol) down to ~6 vol to achieve ≤8.5 wt % of residual iPrOAc (1.1 wt %). The slurry was diluted with n-heptane (42.7 kg, 62.4 L, 6 vol) and stirred at 20-25° C. for 16.0 h before being filtered. The filter cake was washed with heptane (2×28.4 kg, 2×41.5 L, 2×4 vol) and then dried at 40-45° C. for 30 h. Compound A was obtained (9.4 kg, 86% yield, 96.6% AUC by HPLC) as a cream colored solid.

Example 4. Preparation of ARQ 087.2 HCl Crystalline Form D

Starting materials: Compound A
Reagents: 36% Hydrochloric acid (HCl)
Solvents: Acetone
Water (H₂O)

Compound A (9.3 kg, 19.8 mol, 1.0 eq) and acetone (59.1 kg, 74.7 L, 8 vol) were charged to a 100-gallon reactor and the temperature was set to 50-55° C. Once a clear solution was realized, a 1.9 M HCl solution (21.8 L, 41.4 mol, 2.1 eq) was added over a period of 1 h while maintaining a temperature of 50-55° C. When the HCl addition was complete, the mixture was polish filtered into a clean 200-gallon reactor and the temperature was maintained at 50-55° C. Acetone (29.5 kg, 37.3 L, 4 vol) was added to the 200-gallon reactor over a period of 1.75 h before being seeded with a polymorph of Compound A dihydrochloride salt (90.9 g, 1 wt %,). Additional acetone (206 kg, 260.4 L, 28 vol) was added over a period of 4.25 h while maintaining a temperature of 50-55° C. The slurry was cooled to 20-25° C. over a period of 2.5h and stirred for an additional 4.5 h before being filtered. The wet cake was washed with acetone (2×29.9 kg, 2×37.8 L, 2×4 vol) and dried under vacuum at 40-45° C. for 60.0 h. The polymorph of Compound A dihydrochloride salt was obtained (9.3 kg, 87%, 99.2% AUC by HPLC, Lot: 4263.D.13.1) as a yellow solid.

Example 5. Recrystallization of ARQ 087.2 HCl (Form D)

A 50-L reactor was charged with the polymorph of Compound A dihydrochloride salt (1.18 kg) followed by acetone (6.9 kg, 8.7 L, 7.3 vol) and water (2.2 kg, 1.8 vol). The mixture was heated to 50° C. to perform a polish filtration. The filtrate was transferred back to the 50-L reactor, and the temperature was adjusted to 55° C. Acetone (2.8 kg, 3.6 L, 3 vol) was then added at a rate appropriate to maintain an internal temperature of 55° C. Once the addition of acetone was completed, the internal temperature was decreased to 50° C., and the solution was seeded with the polymorph of Compound A dihydrochloride salt, 0.018 kg, 1 wt %). The resulting slurry was stirred at 50° C. for 30 minutes before being cooled to 20° C. over a period of 1 hour. The internal temperature was then increased to 40° C., and acetone (22.9 kg, 29.0 L, 24.5 vol) was added over a period of 1.5 hours, while maintaining an internal temperature of 40° C. The slurry was cooled to 20° C. over a period of 2 hours, and then stirred at 20° C. for 16 hours. The resulting slurry was filtered, and the solids were washed with acetone (2×3.8 kg, 2×4.8 L, 2×4.0 vol). The wet cake was then dried under vacuum at 20° C. for 19 hours. This afforded a polymorph of Compound A dihydrochloride salt as a yellow solid (1.11 kg, 94% yield, 99.7% AUC).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of making a polymorph of Compound A dihydrochloride salt:

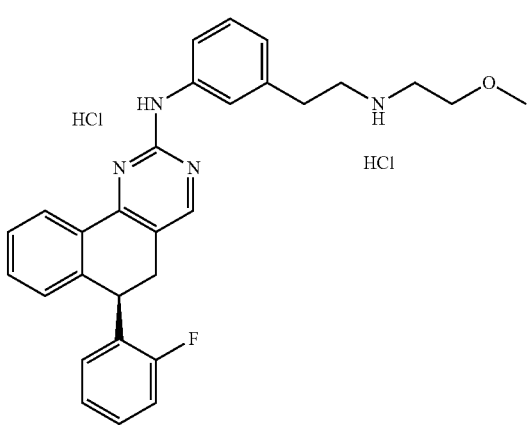

comprising Step 5a:
step 5a-1) reacting Compound A:

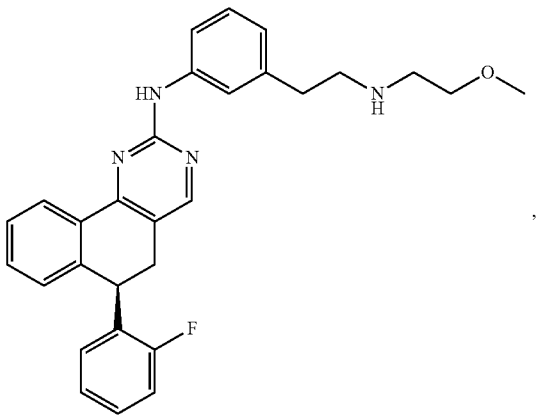 [SMILES: COCCNCCc1cccc(Nc2ncc3c(n2)-c2ccccc2[C@H](c2ccccc2F)C3)c1 ; Cl ; Cl]

(A)

with an aqueous solution of HCl; and
step 5a-4) adding acetone after the reaction between Compound A and HCl, in an amount to achieve a vol/vol ratio of acetone:water of about 95:5.

2. The method of claim 1, wherein step 5a-1) is preceded by dissolving Compound A in acetone.

3. The method of claim 1, wherein Compound A is reacted with HCl at a temperature between about 50° C. and about 55° C.

4. The method of claim 1, further comprising, after step 5a-1) and before step 5a-4), step 5a-3): adding a seed polymorph of Compound A dihydrochloride salt to form a slurry.

5. The method of claim 4, further comprising one or more steps selected from the following: adding acetone to the slurry; cooling the slurry; stirring the slurry; and filtering and drying the slurry to produce a polymorph of Compound A hydrochloride salt.

6. The method of claim 1, further comprising after Step 5a, Step 5b: recrystallizing the polymorph of Compound A dihydrochloride salt.

7. The method of claim 6, wherein Step 5b comprises mixing the polymorph of Compound A dihydrochloride salt with acetone and water.

8. The method of claim 7, further comprising after the mixing, step 5b-1): heating the mixture.

9. The method of claim 8, wherein the mixture is heated to a temperature between about 40° C. and about 55° C.

10. The method of claim 6, further comprising adding a seed polymorph of Compound A dihydrochloride salt to generate a slurry.

11. The method of claim 10, further comprising one or more steps selected from the following: stirring the slurry; cooling the slurry after the stirring; heating the slurry and adding acetone; cooling the slurry after the addition of acetone; and washing and filtering the slurry to produce a polymorph of Compound A dihydrochloride salt.

12. The method of claim 1, further comprising, after step 5a-1) and before step 5a-3), step 5a-2): adding acetone in an amount to achieve a vol/vol ratio of acetone:water of about 84:16.

13. The method of claim 2, wherein after said dissolving Compound A in acetone the vol/vol ratio of acetone:water is about 78:22.

14. The method of claim 7, wherein the vol/vol ratio of acetone:water is about 80:20.

15. The method of claim 8, further comprising after step 5b-1), step 5b-2): adding acetone in an amount to achieve a vol/vol ratio of acetone:water of about 85:15.

16. The method of claim 9, further comprising after step 5b-1), step 5b-2): adding acetone in an amount to achieve a vol/vol ratio of acetone:water of about 85:15.

17. The method of claim 16, further comprising after step 5b-2), adjusting the temperature of the mixture to about 50° C.

18. The method of claim 10, further comprising after adding the seed polymorph, cooling the mixture to a temperature between about 20° C. and about 40° C.

19. The method of claim 10, further comprising after adding the seed polymorph, adding acetone in an amount to achieve a vol/vol ratio of acetone:water of about 95:5.

20. The method of claim 18, further comprising after cooling the mixture, adding acetone in an amount to achieve a vol/vol ratio of acetone:water of about 95:5.

* * * * *